US00PP11647P

United States Patent [19]

Meier et al.

[11] Patent Number: Plant 11,647

[45] Date of Patent: Nov. 28, 2000

[54] KENTUCKY BLUEGRASS DESIGNATED 'BA76-372'

[75] Inventors: Virgil D. Meier, Marysville, Ohio; Jay B. Burr, S. E. Salem, Oreg.

[73] Assignee: OMS Investments, Inc., Wilmington, Del.

[21] Appl. No.: 09/120,718

[22] Filed: Jul. 22, 1998

[51] Int. Cl.[7] ..... A01H 5/00

[52] U.S. Cl. ..... Plt./393

[58] Field of Search ..... Plt./393

[56] References Cited

U.S. PATENT DOCUMENTS

| | | | |
|---|---|---|---|
| P.P. 3,150 | 5/1972 | Pepin et al. | Plt./393 |
| P.P. 3,156 | 5/1972 | Fuchigami et al. | Plt./393 |
| P.P. 3,186 | 5/1972 | Barenbrug et al. | Plt./393 |
| P.P. 4,336 | 11/1978 | Mayer et al. | Plt./393 |
| P.P. 6,280 | 9/1988 | Meier et al. | Plt./393 |
| P.P. 6,537 | 1/1989 | Meier et al. | Plt./393 |
| P.P. 6,538 | 1/1989 | Meier et al. | Plt./393 |
| P.P. 6,585 | 2/1989 | Meier et al. | Plt./393 |
| P.P. 7,831 | 3/1992 | Meier et al. | Plt./393 |
| P.P. 8,490 | 12/1993 | Meier et al. | Plt./393 |
| P.P. 9,036 | 1/1995 | Meier et al. | Plt./393 |
| P.P. 9,209 | 7/1995 | Mayer | Plt./393 |
| P.P. 9,611 | 7/1996 | Meier | Plt./393 |
| P.P. 9,848 | 4/1997 | Meier et al. | Plt./393 |
| P.P. 9,977 | 7/1997 | Meier et al. | Plt./393 |
| P.P. 10,080 | 10/1997 | Meier et al. | Plt./393 |
| P.P. 10,081 | 10/1997 | Meier et al. | Plt./393 |
| P.P. 10,384 | 5/1998 | Meier et al. | Plt./393 |

*Primary Examiner*—Howard J. Locker
*Assistant Examiner*—Wendy Anne Baker
*Attorney, Agent, or Firm*—Jones, Day, Reavis & Pogue

[57] ABSTRACT

A variety of Kentucky bluegrass having a high level of resistance to powdery mildew and a medium to high level of resistance to melting out, leaf spot, and brown patch; a medium green color throughout the growing season; excellent winter color during mild winters; the ability to form a medium quality turf under a wide variety of environmental conditions; a coarse textured turf; and a high level of seed yielding capacity.

3 Drawing Sheets

BACKGROUND OF THE INVENTION

1. Field of the Invention

The present invention relates to a new and distinct variety of *Poa pratensis* that has been designated 'Ba76-372' Kentucky bluegrass.

2. Description of Related Art

Kentucky Bluegrasses have been disclosed in U.S. Plant Pat. No. 3,150, issued May 2, 1972; U.S. Plant Pat. No. 3,156, issued May 9, 1972; U.S. Plant No. 3,186, issued May 23, 1972; U.S. Plant Pat. No. 4,336, issued Nov. 28, 1978: U.S. Plant Pat. No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209, issued Jul. 18, 1995; U.S. Plant Pat. No. 9,611, issued Jul. 23, 1996; U.S. Plant Pat. No. 9,848, issued Apr. 1, 1997: U.S. Plant Pat. No. 9,977, issued Jul. 22, 1997; U.S. Plant Pat. No. 10,080, issued Oct. 21, 1997; U.S. Plant Pat. No. 10,081, issued Oct. 21, 1997; U.S. Plant Pat. No. 10,384, issued May 5, 1998; U.S. Plant Pat. No. 10,925, issued May 25, 1999; and pending U.S. Plant Patent application Ser. No. 09/032,057, filed Feb. 27, 1998, as well as U.S. Plant Patent application Ser. No. 09/120,393, filed Jul. 22, 1998.

SUMMARY OF THE VARIETY

'Ba76-372' plant material originated from a single plant that was a progeny resulting from crossing 'Ba72-482', an unreleased, unpatented Kentucky bluegrass plant grown and maintained in the plant nursery at the Scotts Company in Marysville, Ohio, as the seed parent, with 'Ba72-462', another unreleased, unpatented Kentucky bluegrass plant grown and maintained in the plant nursery at the Scotts Company in Marysville, Ohio, as the pollen parent. As a result of this breeding, a distinct variety was produced and asexually propagated by rhizomes, tillers and disseminules. The highly apomictic seed of 'Ba76-372' Kentucky bluegrass was produced first at Marysville, Ohio, and later at Gervais, Oreg. This seed was used to plant turf performance evaluation trials and later, seed production fields.

Asexual production of 'Ba76-372' initially was performed at Marysville, Ohio, by propagules (tillers and rhizomes) and by disseminules (modified caryopses produced by apomixis) and has consistently produced progeny plants indistinguishable from the first generation asexual reproductions of the instant plant. The apomixis level of 'Ba76-372' is approximately 94.4% (plus or minus 2.1%). The apomixis level was determined by examining seedling characteristics of approximately 100 to 150 seedlings from different crop years in a growth chamber and any seedling with one or more characteristics different from the other 'Ba76-372' seedlings was classified as not being of apomictic origin.

'Ba76-372' has a number of highly desirable characteristics, including a high level of resistance to *Erysiphe graminis* that causes powdery mildew; a medium to high level of resistance to Drechslera spp that causes leaf spot and melting out; and a medium to high level of resistance to *Rhizoctonia solani* that causes brown patch. 'Ba76-372' has an attractive leafy turf type, coarse leaf blades and a medium green color which can be maintained throughout the entire growing season. 'Ba76-372' demonstrates excellent winter color under mild winter conditions.

'Ba76-372' is an overall good turfgrass performer as evidenced by medium scores for quality and color. 'Ba76-372' has a high seed yield potential in the bluegrass seed production region of the northwestern United States.

In comparison with a number of other Kentucky bluegrass varieties, 'Ba76-372' has a significantly longer seed with a shorter rachilla and a significantly higher seed count per pound. The panicle of 'Ba76-372' Kentucky bluegrass is significantly shorter and has a higher number of whorls than several other Kentucky bluegrasses. The peduncle is thicker and the culm is shorter than many other Kentucky bluegrass varieties. It has a flag leaf that is wider and thicker with a longer ligule that has more hairs when compared to most other Kentucky bluegrasses.

DETAILED DESCRIPTION OF THE VARIETY

Figure 1:
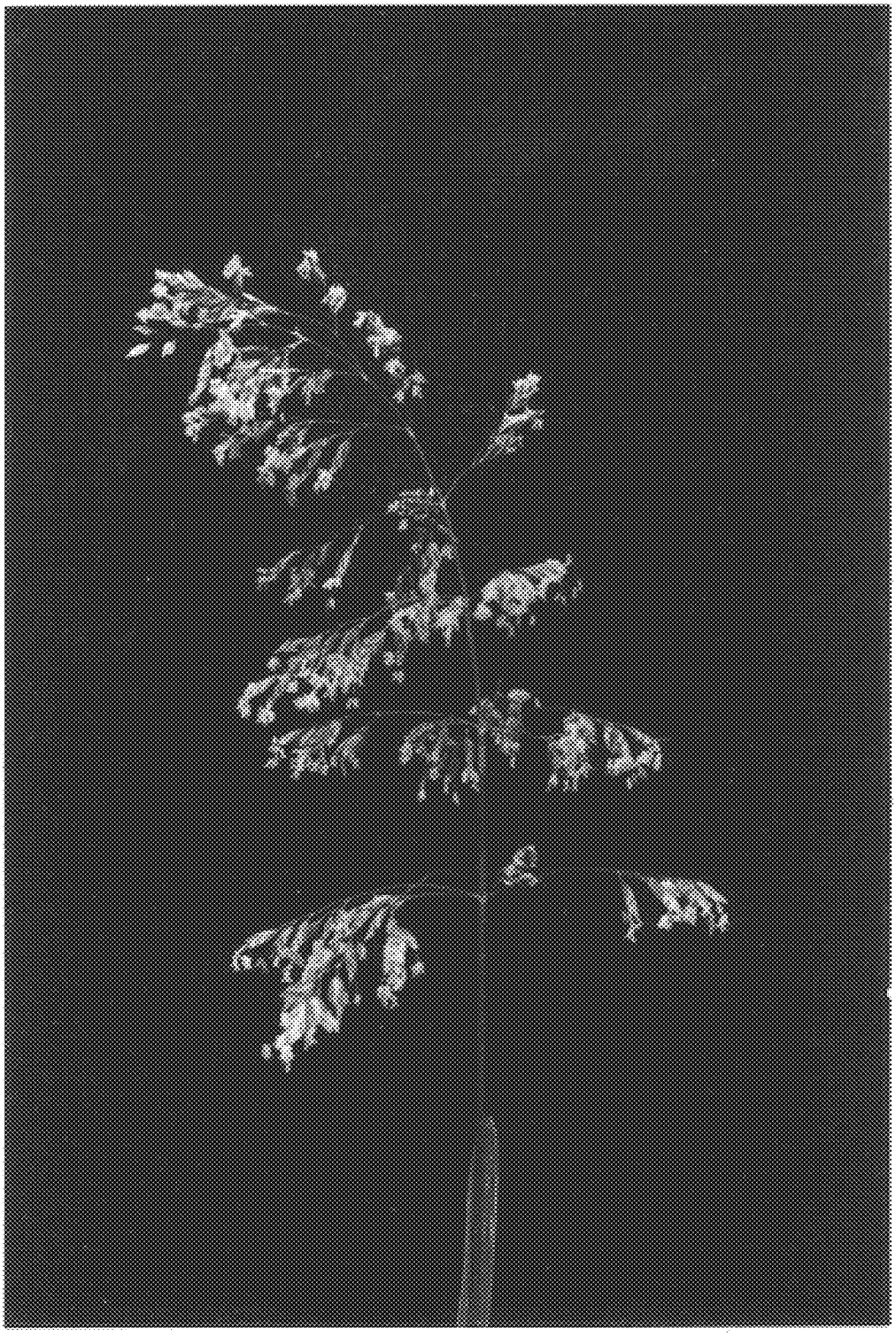
FIG. 1 is a 'Ba76-372' Kentucky bluegrass panicle.
Figure 2:
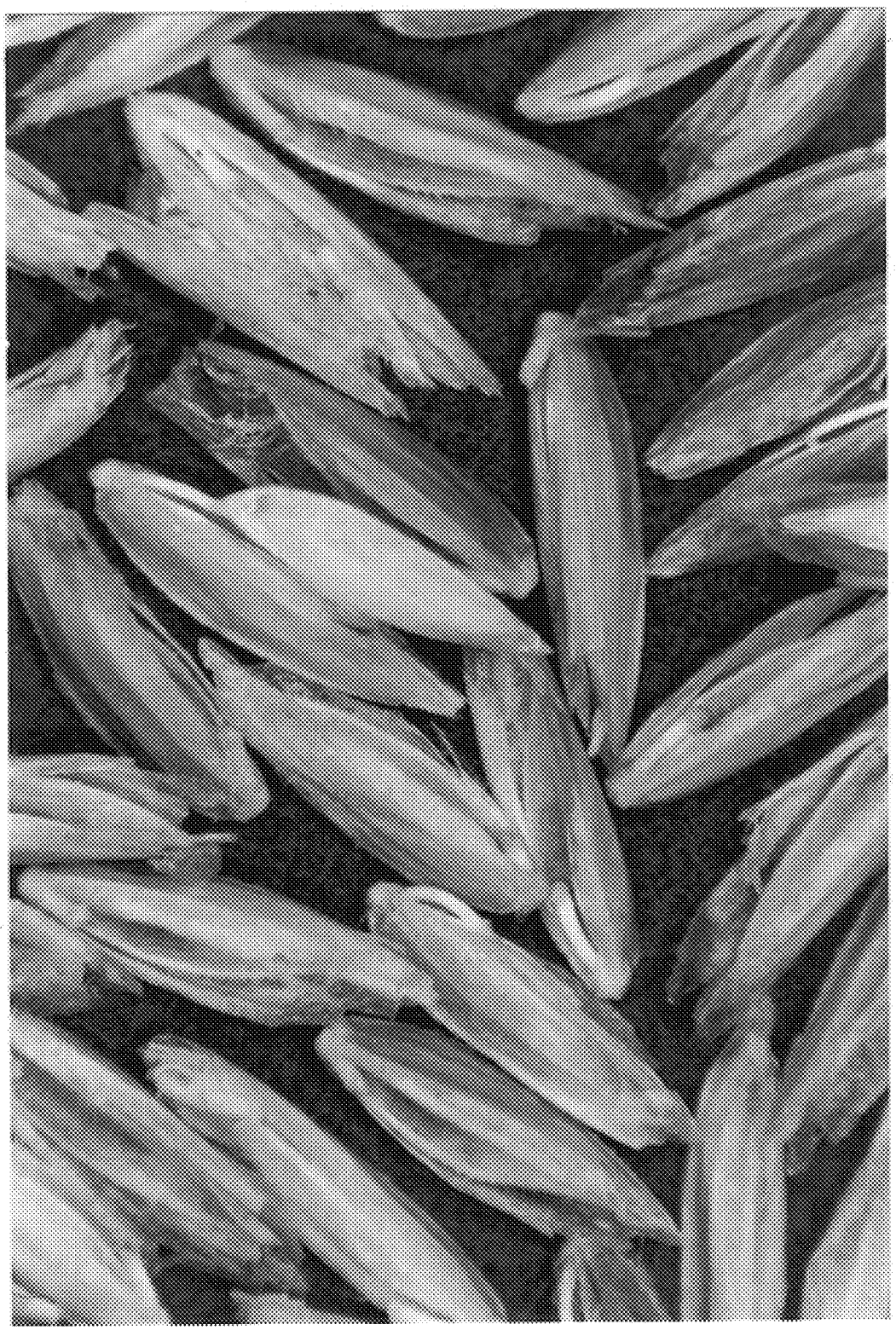
FIG. 2 is a 'Ba76-372' Kentucky bluegrass seed.
Figure 3:
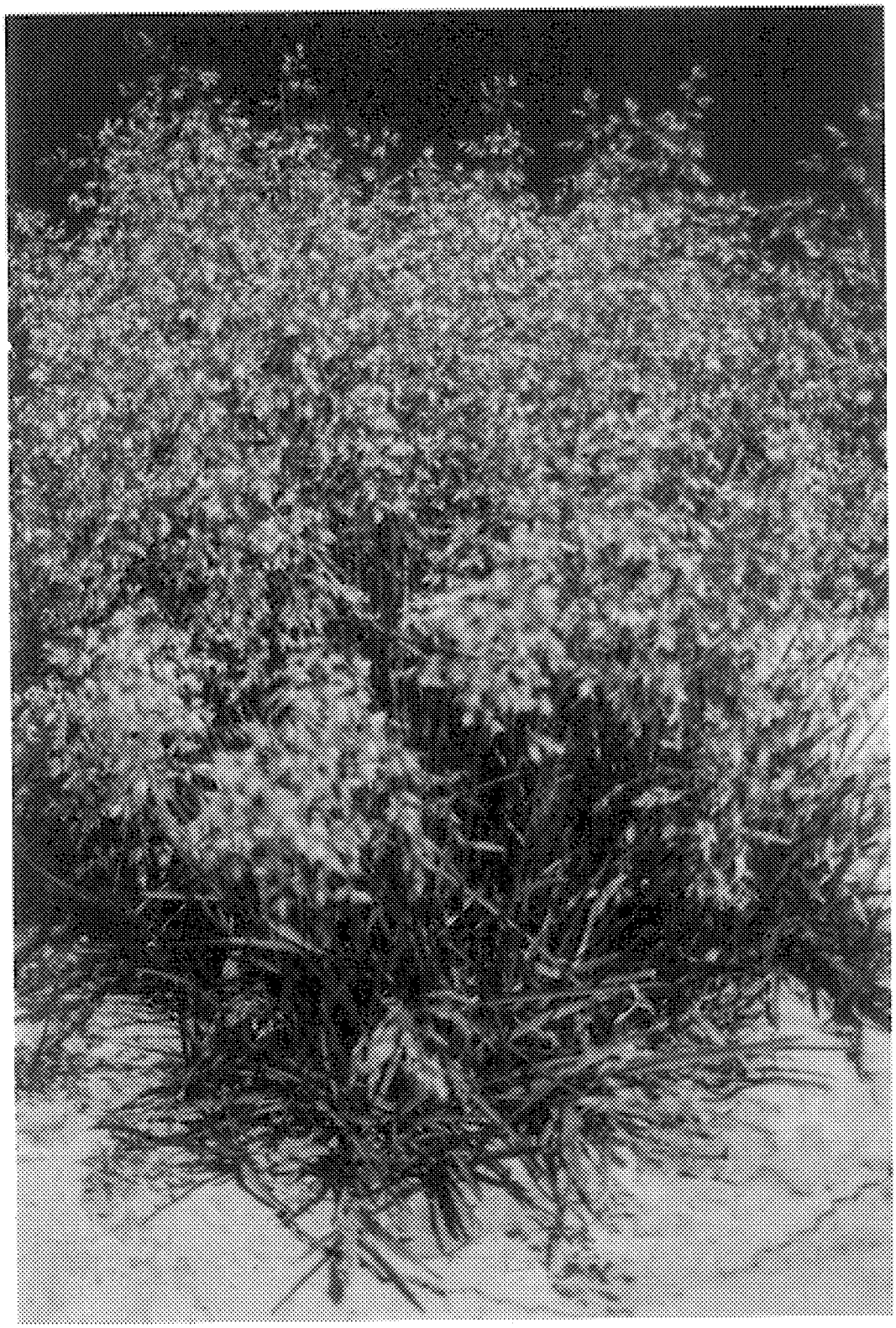
FIG. 3 is a 'Ba76-372' Kentucky bluegrass plant shortly after completing anthesis.

'Ba76-372' Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60–80° F.), culms are erect averaging 38.5 cm in length. The uppermost internode averages 9.0 cm in length. The peduncle averages 26.5 cm in length and 1.27 mm in width. The vegetative leaf averages 27.4 cm in length, 4.3 mm in width, 0.19 mm in thickness and the ligule 0.34 mm in length. The flag leaf averages 5.7 cm in length, 4.2 mm in width, 0.12 mm in thickness and a ligule length of 1.33 mm.

The panicle averages 8.5 cm in length, 7.4 cm in width, and has 6.9 whorls. The lowest whorl and the third whorl from the bottom of the panicle average 4.3 and 4.1 branches, respectively. A spikelet in the lowest whorl averages 4.5 mm in length, 1.9 mm in width, 3.2 florets and the outer glume and inner glume average 2.5 mm and 3.1 mm in length and 0.54 mm and 0.74 mm in width, respectively. A spikelet from the third whorl from the bottom of the panicle averages 5.0 mm in length, 2.1 mm in width, 3.8 florets, and the outer glume and inner glume averages 2.8 mm and 3.4 mm in length and 0.59 mm and 0.82 mm in width, respectively. For the vegetative leaf, the number of hairs is slightly below average for the leaf sheath margin, above average for the dorsal side of the leaf sheath, about average for the upper margin of the ligule, about average for the collar margin and about average for the dorsal side of the leaf. 'Ba76-372' differs significantly from many of the other Kentucky bluegrass varieties in regard to such morphological characteristics as seed length, panicle length, number of whorls per panicle, flag leaf width, flag leaf thickness, flag leaf ligule length, flag leaf ligule hair, peduncle thickness, and culm length.

Since environmental conditions such as soil and climate may influence morphological characteristics to some extent, comparisons of 'Ba76-372' were made with other Kentucky bluegrass varieties under like conditions and the comparisons are set forth in Tables 1–7, as follows.

TABLE 1

Morphological Comparisons of Peduncles, Culms, and Top Internodes of 'Ba76-372' with Other Kentucky Bluegrass Varieties in the Greenhouse at Marysville, Ohio.

| Variety | Peduncle Length (cm) | Peduncle Thickness (mm) | Culm Length (cm) | Top Internode Length (cm) |
|---|---|---|---|---|
| 'Ba76-372' | 26.54 | 1.27 | 38.52 | 9.00 |
| 'Ba79-260' | 26.39 | 0.91 | 54.11 | 11.10 |
| 'Abbey' | 26.83 | 0.99 | 33.30 | 7.40 |
| 'Ascot' | 18.76 | 0.67 | 38.25 | 5.79 |
| 'Famous' | 20.99 | 1.04 | 48.88 | 8.85 |
| 'Goldrush' | 19.26 | 0.89 | 43.05 | 7.44 |
| 'Nottingham' | 26.70 | 1.19 | 39.20 | 9.42 |
| 'Raven' | 26.12 | 0.78 | 55.32 | 11.64 |
| 'Sidekick' | 27.22 | 0.91 | 55.88 | 10.36 |
| LSD (.05) | 2.76 | 0.11 | 3.64 | 1.56 |

TABLE 2

Morphological Comparisons of Vegetative Leaves of 'Ba76-372' and Other Kentucky Bluegrass Varieties in the Greenhouse at Marysville, Ohio.

| Variety | Length (cm) | Width (mm) | Thickness (mm) | Ligule Length (mm) |
|---|---|---|---|---|
| 'Ba76-372' | 27.39 | 4.33 | 0.19 | 0.34 |
| 'Ba79-260' | 25.81 | 4.65 | 0.19 | 0.36 |
| 'Abbey' | 23.42 | 4.02 | 0.20 | 0.40 |
| 'Ascot' | 28.41 | 3.84 | 0.19 | 0.31 |
| 'Famous' | 27.46 | 4.58 | 0.21 | 0.41 |
| 'Goldursh' | 20.80 | 3.89 | 0.19 | 0.40 |
| 'Nottingham' | 26.46 | 4.78 | 0.20 | 0.40 |
| 'Raven' | 24.44 | 4.62 | 0.21 | 0.37 |
| 'Sidekick' | 29.03 | 4.94 | 0.21 | 0.48 |
| LSD (.05) | 3.54 | 0.45 | 0.01 | 0.05 |

TABLE 3

Morphological Comparisons of Flag Leaves of 'Ba76-372' and Other Kentucky Bluegrass Varieties in the Greenhouse at Marysville, Ohio.

| Variety | Length (cm) | Width (mm) | Thickness (mm) | Ligule Length (mm) | Ligule Hair* |
|---|---|---|---|---|---|
| 'Ba76-372' | 5.66 | 4.21 | 0.122 | 1.33 | 2.20 |
| 'Ba79-260' | 6.90 | 3.55 | 0.104 | 1.11 | 0.90 |
| 'Abbey' | 3.57 | 2.99 | 0.109 | 0.91 | 1.60 |
| 'Ascot' | 6.03 | 2.49 | 0.102 | 1.15 | 1.60 |
| 'Famous' | 7.65 | 3.83 | 0.102 | 1.19 | 1.38 |
| 'Goldrush' | 7.11 | 3.21 | 0.089 | 1.00 | 2.00 |
| 'Nottingham' | 4.77 | 3.71 | 0.124 | 1.08 | 2.30 |
| 'Raven' | 5.87 | 3.38 | 0.104 | 1.08 | 1.20 |
| 'Sidekick' | 6.65 | 3.61 | 0.104 | 1.07 | 1.10 |
| LSD (.05) | 1.13 | 0.47 | 0.013 | 0.163 | 0.49 |

*Rating 0–9;
0 = None;
9 = Many Hairs.

TABLE 4

Morphological Comparisons for Panicle Length and Width, Whorl Number and Whorl Branches of 'Ba76-372' and Other Kentucky Bluegrass Varieties Grown in the Greenhouse in Marysville, Ohio.

| | Panicle | | | Number of Branches | |
|---|---|---|---|---|---|
| Variety | Length (cm) | Width (cm) | Whorl No. | Lowest Whorl | Third Whorl |
| 'Ba76-372' | 8.51 | 7.44 | 6.90 | 4.3 | 4.10 |
| 'Ba79-260' | 8.88 | 7.53 | 5.30 | 4.0 | 3.60 |
| 'Abbey' | 6.04 | 4.99 | 5.80 | 3.7 | 3.30 |
| 'Ascot' | 10.03 | 7.01 | 4.20 | 2.2 | 2.00 |
| 'Famous' | 12.11 | 8.11 | 6.22 | 4.2 | 3.78 |
| 'Goldrush' | 10.25 | 6.63 | 5.70 | 3.6 | 3.50 |
| 'Nottingham' | 8.08 | 7.15 | 7.00 | 4.4 | 4.40 |
| 'Raven' | 8.15 | 6.36 | 5.30 | 4.0 | 3.20 |
| 'Sidekick' | 11.22 | 3.52 | 5.50 | 2.8 | 2.60 |
| LSD (.05) | 0.92 | 1.21 | 0.61 | 0.6 | 0.53 |

TABLE 5

Morphological Comparisons of Spikelets and Florets of 'Ba76-372' and Other Kentucky Bluegrass Varieties in the Greenhouse at Marysville, Ohio.

| | Spikelet | | | | | |
|---|---|---|---|---|---|---|
| | Lowest Whorl | | Third Whorl | | No. of Florests per Spikelet | |
| Variety | Length (mm) | Width (mm) | Length (mm) | Width (mm) | Lowest Whorl | Third Whorl |
| 'Ba76-372' | 4.45 | 1.92 | 4.96 | 2.09 | 3.2 | 3.8 |
| 'Ba79-260' | 5.03 | 2.01 | 5.16 | 2.31 | 3.9 | 4.3 |
| 'Abbey' | 4.67 | 1.85 | 4.54 | 1.94 | 3.1 | 3.1 |
| 'Ascot' | 5.34 | 2.03 | 5.10 | 2.06 | 3.2 | 2.9 |
| 'Famous' | 5.19 | 2.14 | 5.18 | 2.09 | 4.0 | 3.9 |
| 'Goldrush' | 4.71 | 1.69 | 4.96 | 1.89 | 3.0 | 3.6 |
| 'Nottingham' | 5.69 | 2.33 | 5.22 | 2.47 | 4.4 | 3.7 |
| 'Raven' | 4.63 | 2.11 | 4.75 | 2.04 | 3.9 | 3.8 |
| 'Sidekick' | 5.08 | 2.67 | 5.23 | 2.71 | 4.1 | 4.6 |
| LSD (.05) | 0.491 | 0.301 | 0.432 | 0.36 | 0.6 | 0.6 |

TABLE 6

Morphological Comparisons of Glume Size of 'Ba76-372' and Other Kentucky Bluegrass Varieties in the Greenhouse at Marysville, Ohio.

| | Outer Glume | | | |
|---|---|---|---|---|
| | Lowest Whorl | | Third Whorl | |
| Variety | Length (mm) | Width (mm) | Length (mm) | Width (mm) |
| 'Ba76-372' | 2.51 | 0.54 | 2.79 | 0.59 |
| 'Ba79-260' | 2.79 | 0.55 | 3.05 | 0.53 |
| 'Abbey' | 2.51 | 0.53 | 2.52 | 0.46 |
| 'Ascot' | 3.92 | 0.50 | 3.74 | 0.56 |
| 'Famous' | 2.99 | 0.56 | 2.91 | 0.64 |
| 'Goldrush' | 2.65 | 0.51 | 3.07 | 0.62 |
| 'Nottingham' | 2.99 | 0.61 | 2.91 | 0.57 |
| 'Raven' | 2.85 | 0.53 | 2.87 | 0.47 |
| 'Sidekick' | 3.27 | 0.52 | 3.41 | 0.63 |
| LSD (.05) | 0.31 | 0.10 | 0.30 | 0.11 |

TABLE 6-continued

Morphological Comparisons of Glume Size of 'Ba76-372' and Other Kentucky Bluegrass Varieties in the Greenhouse at Marysville, Ohio.

| | Inner Glume | | | |
|---|---|---|---|---|
| | Lowest Whorl | | Third Whorl | |
| Variety | Length (mm) | Width (mm) | Length (mm) | Width (mm) |
| 'Ba76-372' | 3.10 | 0.74 | 3.35 | 0.82 |
| 'Ba79-260' | 3.07 | 0.74 | 3.33 | 0.73 |
| 'Abbey' | 2.96 | 0.69 | 3.00 | 0.69 |
| 'Ascot' | 4.13 | 0.71 | 4.03 | 0.68 |
| 'Famous' | 3.38 | 0.74 | 3.36 | 0.73 |
| 'Goldrush' | 3.41 | 0.76 | 3.70 | 0.81 |
| 'Nottingham' | 3.31 | 0.81 | 3.33 | 0.67 |
| 'Raven' | 3.11 | 0.74 | 3.09 | 0.68 |
| 'Sidekick' | 3.51 | 0.65 | 3.69 | 0.73 |
| LSD (.05) | 0.29 | 0.14 | 0.28 | 0.12 |

TABLE 7

Morphological Comparisons of the Level of Hairs on the Vegetative Leaves of 'Ba76-372' and Other Kentucky Bluegrass Varieties in the Greenhouse at Marysville, Ohio.

| Variety | Leaf Sheath Margin | Leaf Sheath Dorsal | Ligule Upper Margin | Collar Margin | Leaf Dorsal |
|---|---|---|---|---|---|
| 'Ba76-372' | 2.30 | 2.3 | 5.3 | 3.3 | 1.0 |
| 'Ba79-260' | 1.80 | 1.0 | 3.1 | 2.2 | 1.0 |
| 'Abbey' | 3.10 | 2.7 | 6.3 | 3.6 | 1.0 |
| 'Ascot' | 2.10 | 1.0 | 2.0 | 4.4 | 0.0 |
| 'Famous' | 2.80 | 1.4 | 4.3 | 3.3 | 1.0 |
| 'Goldrush' | 3.40 | 1.0 | 4.6 | 2.2 | 1.0 |
| 'Nottingham' | 3.30 | 3.6 | 7.1 | 4.4 | 1.0 |
| 'Raven' | 1.80 | 1.1 | 3.1 | 2.1 | 1.0 |
| 'Sidekick' | 2.10 | 1.2 | 2.3 | 3.6 | 0.0 |
| LDS (0.5) | 0.55 | 0.4 | 0.7 | 0.7 | 0.1 |

Rating Scale: 0–9;
0 = None;
9 = Many Hairs.

The seed of 'Ba76-372' was conditioned by removing most of the extraneous materials that may have been harvested with the seed, such as small pieces of plant stems and leaves, soil particles, seed of other plants, hair attached to the seed and the like. This conditioned seed of 'Ba76-372' averages 3.19 mm in length, 0.87 mm in width, and a rachilla length of 0.56 mm. It has an average level of hairs at the base of the lemma. 'Ba76-372' has about 1,127,400 seeds per pound.

Comparisons of 'Ba76-372' with other Kentucky bluegrass varieties in terms of seed numbers per pound and other seed characteristics are shown in Tables 8–9 as follows:

TABLE 8

Morphological Comparisons of Seed Length, Width, Rachilla Length and Lemma Hairs of 'Ba76-372' and Other Kentucky Bluegrass Varieties after Conditioning.

| Variety | Length (mm) | Width (mm) | Rachilla (mm) | Lemma Hairs[1/] |
|---|---|---|---|---|
| 'Ba76-372' | 3.19 | 0.87 | 0.56 | 2.11 |
| 'Ba79-260' | 2.77 | 0.79 | 0.82 | 2.33 |
| 'Abbey' | 3.02 | 0.85 | 0.56 | 1.80 |
| 'Ascot' | 3.00 | 0.81 | 0.68 | 6.30 |

TABLE 8-continued

Morphological Comparisons of Seed Length, Width, Rachilla Length and Lemma Hairs of 'Ba76-372' and Other Kentucky Bluegrass Varieties after Conditioning.

| Variety | Length (mm) | Width (mm) | Rachilla (mm) | Lemma Hairs[1/] |
|---|---|---|---|---|
| 'Famous' | 3.02 | 0.86 | 0.65 | 1.56 |
| 'Goldrush' | 2.80 | 0.75 | 0.81 | 1.22 |
| 'Nottingham' | 3.02 | 0.84 | 0.69 | 1.10 |
| 'Raven' | 2.88 | 0.80 | 0.67 | 2.50 |
| 'Sidekick' | 2.84 | 0.84 | 0.88 | 2.11 |
| LSD (.05) | 0.20 | 0.11 | 0.21 | 0.70 |

[1/]Rating Scale 0–9;
0 = None;
9 = Most Hairs.

TABLE 9

Comparison of Seeds Per Pound of 'Ba76-372' and Other Kentucky Bluegrass Varieties After Conditioning.

| Variety | Seeds per Pound |
|---|---|
| 'Ba76-372' | 1,127,400 |
| 'Ba79-260' | 1,038,300 |
| 'Abbey' | 1,003,000 |
| 'Ascot' | 1,039,400 |
| 'Coventry' | 1,374,700 |
| 'Famous' | 1,128,600 |
| 'Goldrush' | 942,700 |
| 'Nottingham' | 1,066,000 |
| 'Raven' | 1,127,100 |
| 'Sidekick' | 928,000 |
| LSD (.05) | 38,080 |

'Ba76-372' has performed well throughout the U.S. as exhibited by medium turf quality ratings in comparison with other Kentucky bluegrass varieties. In addition, it has a medium green color which can be maintained throughout the growing season.

With regard to a comparative analysis conducted for purposes of determining color of 'Ba76-372' plants relative to other Kentucky bluegrass varieties, readings were taken of the vegetative color of 'Ba76-372' during mid-October while the turf was actively growing with adequate nutrient and water availability. The readings were taken in full sun with several actively growing leaves being compared, one at a time, utilizing color chips from the Munsell Book of Color as a reference. On this basis, the color of 'Ba76-372' was determined to be 7.5 GY 4/4. During the same time period, the color of similar leaves of other Kentucky bluegrass varieties were determined by the same procedure to be as follows: Ascot — 5 GY 4/4; Buckingham — 7.5 GY 4/4; 'Nottingham' — 5 GY 4/6; 'Midnight' — 7.5 GY 4/4; 'Abbey' — 5 GY 4/6; and Victa — 5 GY 4/4. However, it should be noted that the general apparent color of turf does not always correlate directly with the color of the individual actively growing leaves within the turf and that turf color varies with nutrient level and time of year with some varieties being darker or lighter green, depending on such factors.

Comparisons of 'Ba76-372' with other Kentucky bluegrass varieties for quality, genetic color, spring greenup, winter color, turf density, leaf texture, and seed yield are set forth hereinafter in Tables 10–17 as follows.

TABLE 10

A Comparison of Quality of 'Ba76-372' and Other Kentucky Bluegrass Varieties as Affected by Environmental Conditions.

| Variety | Dense Shade[1/] | Full Sun[2/] |
|---|---|---|
| 'Ba76-372' | 4.4 | 5.4 |
| 'Ba79-260' | 4.7 | 5.8 |
| 'Abbey' | 4.2 | 5.6 |
| 'Ascot' | 5.4 | 5.6 |
| 'Baron' | 3.7 | 5.5 |
| 'Chateau' | 5.3 | 6.0 |
| 'Classic' | 4.7 | 5.8 |
| 'Coventry' | 5.1 | 5.9 |
| 'Eclipse' | 4.6 | 5.8 |
| 'Glade' | 4.4 | 6.0 |
| 'Goldrush' | 4.7 | 5.6 |
| 'Kenblue' | 3.2 | 4.9 |
| 'Limousine' | 4.8 | 6.0 |
| 'Midnight' | 3.2 | 6.3 |
| 'Raven' | 3.4 | 5.7 |
| 'Sidekick' | 4.3 | 5.1 |
| LSD (.05) | 1.6 | 0.2 |

Rating Scale: 0–9;
9 = Excellent.
[1/]From Maryland
[2/]From 29 different locations in the US

TABLE 11

A Comparison of Quality of 'Ba76-372' and Other Kentucky Bluegrass Varieties as Affected by Climatic Regions in the U.S.

| Variety | Transition Zone[1/] | Cool-Arid[2/] | Cool-Humid[3/] |
|---|---|---|---|
| 'Ba76-372' | 5.0 | 5.7 | 5.6 |
| 'Ba79-260-2 | 5.5 | 5.3 | 6.1 |
| 'Abbey' | 5.4 | 5.7 | 5.7 |
| 'Ascot' | 5.2 | 5.6 | 5.8 |
| 'Baron' | 5.5 | 5.7 | 5.5 |
| 'Chateau' | 5.7 | 6.0 | 6.1 |
| 'Classic' | 5.3 | 6.0 | 6.1 |
| 'Coventry' | 5.7 | 5.5 | 6.2 |
| 'Eclipse' | 5.5 | 5.5 | 6.0 |
| 'Glade' | 5.8 | 6.1 | 6.1 |
| 'Goldrush' | 5.5 | 5.6 | 5.7 |
| 'Kenblue' | 4.8 | 5.3 | 4.9 |
| 'Limousine' | 5.7 | 6.1 | 6.3 |
| 'Midnight' | 6.1 | 6.3 | 6.5 |
| 'Raven' | 5.6 | 5.6 | 5.8 |
| 'Sidekick' | 5.0 | 5.4 | 5.1 |
| LSD (.05) | 0.3 | 0.5 | 0.2 |

Rating Scale: 0–9;
9 = Excellent.
[1/]From 10 different locations in the U.S.
[2/]From 16 different locations in the U.S.
[3/]From 3 different locations in the U.S.

TABLE 12

A Comparison of Genetic Color, Spring Greenup and Winter Color of 'Ba76-372' and Other Kentucky Bluegrass Varieties.

| Variety | Genetic Color[1/] | Spring Greenup[2/] | Winter Color[3/] |
|---|---|---|---|
| 'Ba76-372' | 6.5 | 5.6 | 5.8 |
| 'Ba79-260' | 7.6 | 5.4 | 5.8 |
| 'Abbey' | 6.4 | 5.6 | 5.0 |
| 'Ascot' | 7.1 | 5.1 | 4.5 |
| 'Baron' | 6.4 | 5.5 | 5.2 |
| 'Chateau' | 6.2 | 5.6 | 5.0 |
| 'Classic' | 5.8 | 6.4 | 6.0 |
| 'Coventry' | 6.4 | 5.6 | 4.7 |

TABLE 12-continued

A Comparison of Genetic Color, Spring Greenup and Winter Color of 'Ba76-372' and Other Kentucky Bluegrass Varieties.

| Variety | Genetic Color[1/] | Spring Greenup[2/] | Winter Color[3/] |
|---|---|---|---|
| 'Eclipse' | 6.5 | 5.6 | 5.3 |
| 'Glade' | 6.8 | 5.7 | 5.3 |
| 'Goldrush' | 6.4 | 5.5 | 4.8 |
| 'Kenblue' | 5.4 | 6.2 | 5.3 |
| 'Limousine' | 6.3 | 5.5 | 4.3 |
| 'Midnight' | 7.7 | 5.6 | 5.7 |
| 'Raven' | 6.2 | 5.6 | 4.5 |
| 'Sidekick' | 6.3 | 5.5 | 5.2 |
| LSD (.05) | 0.2 | 0.3 | 0.8 |

Ratings 1–9;
9 = Dark Green, Faster Greening.
[1/]From 27 different locations in the U.S.
[2/]From 14 different locations in the U.S.
[3/]From 2 different locations in the U.S.

TABLE 13

A Comparison of Turf Density of 'Ba76-372' and Other Kentucky Bluegrass Varieties.

| | Turf Density | | |
|---|---|---|---|
| Variety | Spring[1/] | Summer[2/] | Fall[3/] |
| 'Ba76-372' | 5.5 | 6.2 | 6.6 |
| 'Ba79-260' | 5.9 | 6.6 | 6.7 |
| 'Abbey' | 6.0 | 6.4 | 6.4 |
| 'Ascot' | 5.7 | 6.5 | 6.6 |
| 'Baron' | 5.8 | 6.3 | 6.4 |
| 'Chateau' | 6.1 | 6.8 | 6.8 |
| 'Classic' | 6.2 | 7.0 | 6.9 |
| 'Coventry' | 6.1 | 6.5 | 7.0 |
| 'Eclipse' | 5.8 | 6.5 | 6.7 |
| 'Glade' | 6.4 | 6.8 | 7.0 |
| 'Goldrush' | 5.9 | 6.5 | 6.5 |
| 'Kenblue' | 5.8 | 6.5 | 6.5 |
| 'Limousine' | 6.7 | 7.0 | 7.3 |
| 'Midnight' | 6.3 | 6.7 | 7.0 |
| 'Raven' | 6.1 | 6.7 | 6.3 |
| 'Sidekick' | 5.3 | 6.1 | 6.2 |
| LSD (.05) | 0.4 | 0.5 | 0.3 |

Density Rating: 1–9;
9 = maximum density.
[1/]From 8 different locations in the U.S.
[2/]From 9 different locations in the U.S.
3/From 12 different locations in the U.S.

TABLE 14

A Comparison of Leaf Texture of 'Ba76-372' and Other Kentucky Bluegrass Varieties.

| Variety | Leaf Texture[1/] |
|---|---|
| 'Ba76-372' | 5.3 |
| 'Ba79-260' | 6.1 |
| 'Abbey' | 5.7 |
| 'Ascot' | 6.1 |
| 'Baron' | 5.7 |
| 'Chateau' | 5.5 |
| 'Classic' | 6.2 |
| 'Coventry' | 5.6 |
| 'Eclipse' | 6.1 |
| 'Glade' | 6.6 |
| 'Goldrush' | 6.0 |
| 'Kenblue' | 7.0 |
| 'Limousine' | 7.3 |
| 'Midnight' | 6.4 |

TABLE 14-continued

A Comparison of Leaf Texture of 'Ba76-372' and Other Kentucky Bluegrass Varieties.

| Variety | Leaf Texture[1/] |
|---|---|
| 'Raven' | 5.6 |
| 'Sidekick' | 5.0 |
| LSD (.05) | 0.2 |

Texture Rating: 1–9;
9 = fine texture.
[1/]From 23 different locations in the U.S.

TABLE 15

A Comparison of Seed Yield (Pounds per Acre) of 'Ba76-372' and Other Kentucky Bluegrass Varieties in Two (2) Tests Conducted at Gervais, Oregon.

| Variety | Test 1 | Test 2 |
|---|---|---|
| 'Ba76-372' | 913 | 890 |
| 'Abbey' | 516 | 848 |
| 'Buckingham' | 457 | 1071 |
| 'Coventry' | 480 | 429 |
| 'Goldrush' | 514 | 785 |
| 'Midnight' | 112 | 618 |
| 'Sidekick' | 1196 | 982 |
| 'Vantage' | 328 | 663 |
| LSD (.05) | 100 | 130 |

TABLE 16

A Comparison of Seed Yield (Pounds per Acre) of 'Ba76-372' and Other Kentucky Bluegrass Varieties at LaGrande, Oregon.

| Variety | |
|---|---|
| 'Ba76-372' | 1193 |
| 'Ba79-260' | 1182 |
| 'Abbey' | 1484 |
| 'Coventry' | 915 |
| 'Goldrush' | 1165 |
| LSD (.05) | 200 |

TABLE 17

A Comparison of Seed Yield (Pounds per Acre) of 'Ba76-372' and Other Kentucky Bluegrass Varieties in Two (2) Tests Conducted at Connell, Oregon.

| Variety | Test 1 | Test 2 |
|---|---|---|
| 'Ba76-372' | 1518 | 1467 |
| 'Abbey' | 2026 | 1493 |
| 'Able 1' | 1137 | 656 |
| 'Allure' | 1053 | 895 |
| 'Ascot' | 1086 | 831 |
| 'Bristo'l | 1107 | 1060 |
| 'Buckingham' | 813 | 1017 |
| 'Cobalt' | 682 | 857 |
| 'Goldrush' | 1513 | 1319 |
| 'Sidekick' | 844 | 880 |
| LSD (.05) | 217 | 268 |

Turf diseases are one of the major causes of inconsistent and poor turf performance. 'Ba76-372' has been found to have a medium to high level of resistance to powdery mildew caused by *Erysiphe graminis*; melting out and leaf spot caused by *Drechslera poae* (formerly called *Helminthosporium vagans*); and brown patch caused by *Rhizoctonia solani.*

Comparisons of disease incidence of 'Ba76-372' as compared with other Kentucky bluegrass varieties in regard to leaf spot, summer patch, powdery mildew, melting out and brown patch are presented in Table 18 as follows:

TABLE 18

A Comparison of Diseases of 'Ba76-372' and Other Kentucky Bluegrass Varieties.

| Variety | Leaf Spot[1/] | Summer Patch[2/] | Powdery Mildew[3/] | Melting Out[4/] | Brown Patch[5/] |
|---|---|---|---|---|---|
| 'Ba76-372' | 5.7 | 2.3 | 8.7 | 6.0 | 6.2 |
| 'Ba79-260' | 6.0 | 7.3 | 8.3 | 7.0 | 6.7 |
| 'Abbey' | 3.4 | 6.7 | 6.7 | 6.0 | 3.8 |
| 'Ascot' | 6.9 | 5.7 | 8.7 | 8.0 | 6.7 |
| 'Baron' | 4.1 | 6.3 | 6.0 | 4.8 | 4.0 |
| 'Chateau' | 5.6 | 5.0 | 8.7 | 7.0 | 4.7 |
| 'Classic' | 6.3 | 7.3 | 8.3 | 6.3 | 5.3 |
| 'Coventry' | 5.3 | 6.7 | 8.7 | 7.0 | 6.8 |
| 'Eclipse' | 5.7 | 8.7 | 8.7 | 7.0 | 6.5 |
| 'Glade' | 4.8 | 6.7 | 6.7 | 7.2 | 4.8 |
| 'Goldrush' | 3.8 | 6.0 | 7.0 | 5.3 | 5.0 |
| 'Kenblue' | 3.2 | 4.0 | 8.3 | 1.3 | 2.8 |
| 'Limousine' | 6.3 | 7.0 | 8.7 | 7.7 | 5.7 |

TABLE 18-continued

A Comparison of Diseases of 'Ba76-372' and Other Kentucky Bluegrass Varieties.

| Variety | Leaf Spot[1/] | Summer Patch[2/] | Powdery Mildew[3/] | Melting Out[4/] | Brown Patch[5/] |
|---|---|---|---|---|---|
| 'Midnight' | 6.9 | 6.7 | 5.3 | 7.8 | 7.2 |
| 'Raven' | 3.5 | 6.3 | 6.7 | 6.5 | 4.8 |
| 'Sidekick' | 4.4 | 8.0 | 8.0 | 4.5 | 3.3 |
| LSD (.05) | 1.7 | 1.8 | 1.4 | 1.1 | 2.3 |

Rating Scale: 1–9;
9 = No Disease.
[1/]From Maine
[2/]From New Jersey
[3/]From Maryland
[4/]From Maryland and Pennsylvania
[5/]From Maine

What is claimed is:

1. A new and distinct variety of Kentucky bluegrass plant, as herein illustrated and described.

* * * * *